United States Patent [19]

Olsen

[11] Patent Number: 5,483,166
[45] Date of Patent: Jan. 9, 1996

[54] ELECTROCHEMICAL TEST CELL FOR CONDUCTIVITY AND TRANSPORT MEASUREMENTS

[76] Inventor: Ib I. Olsen, Bloommegrenen 159, 5220 Odense, Denmark

[21] Appl. No.: 42,315

[22] Filed: Apr. 2, 1993

[51] Int. Cl.⁶ .................................................. G01N 27/07
[52] U.S. Cl. .......................... 324/450; 324/446; 324/448; 324/449
[58] Field of Search .................................... 324/439, 446, 324/448, 449, 450, 722; 204/157.15

[56] References Cited

U.S. PATENT DOCUMENTS

| | | | |
|---|---|---|---|
| 2,486,432 | 11/1949 | Otto | 324/450 |
| 2,910,647 | 10/1959 | Kreitsek et al. | 324/446 X |
| 4,203,807 | 5/1980 | Buchholz | 324/439 X |
| 4,427,945 | 1/1984 | Sperry | 324/446 |
| 4,803,869 | 2/1989 | Barcelona et al. | 324/439 X |
| 5,124,654 | 6/1992 | Scheid | 324/446 X |
| 5,408,184 | 4/1995 | Moulton | 324/450 |

*Primary Examiner*—Kenneth A. Wieder
*Assistant Examiner*—Glenn W. Brown

[57] ABSTRACT

An electrochemical test cell for measuring conductivity and transport properties of a solid or liquid electrolyte comprises a longitudinal chamber, produced, e.g., from a syringe, a pair of electrodes and means for holding the electrodes which defines an adjustable volume for containing the electrolyte and which aids in maintaining contact between the electrolyte and the electrode.

22 Claims, 1 Drawing Sheet

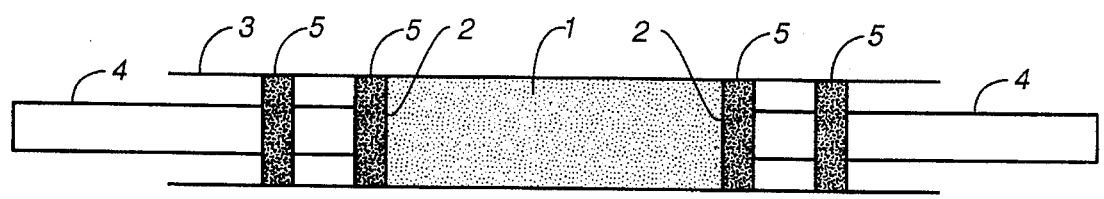
FIG._1
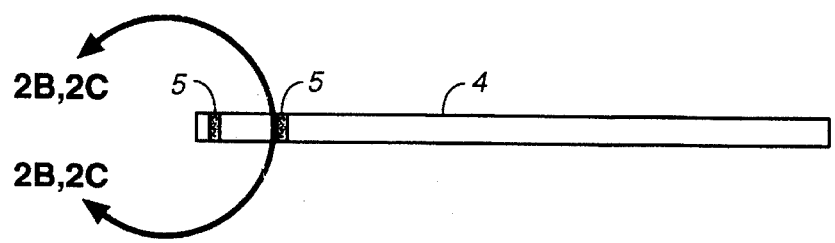
FIG._2A
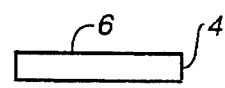   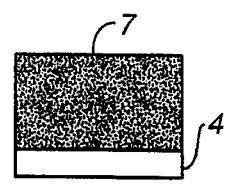
FIG._2B   FIG._2C

ELECTROCHEMICAL TEST CELL FOR CONDUCTIVITY AND TRANSPORT MEASUREMENTS

FIELD OF THE INVENTION

The present invention relates to an electrochemical test cell for use in conductivity and/or transport measurements. The improved test cell according to the present invention is capable of being employed with both liquid and solid electrolytes.

BACKGROUND OF THE INVENTION

Conductivity cells are a well recognized means for measuring the conductivity of electrolytes. Electrolytic conductance is the transport of electric charge under electric potential differences by particles of atomic or larger size. This phenomenon is distinguished from electronic or metallic conductance which is due to the movement of electrons. Electrolytic conductors may be solids, liquids or gases.

Conductance is usually measured as the specific conductance, $\kappa$, which is the reciprocal of the resistance of a cube of material, 1 cm in each direction, placed between electrodes 1 $cm^2$, on opposite sides of the cube.

Conductances of solutions and solids are usually measured by the Kohlrausch method in which a Wheatstone bridge is employed. The conductance cell containing the electrolytic conductor between electrodes is placed is one arm of the bridge. By using an alternating current between the electrodes of the cell, the electrochemical reactions are reversed on the half cycle. When a small alternating current is used for input signal to the electrodes, practically all the electric charge passed during each half cycle is stored in electric double layer which acts as a capacitor.

However, traditional conductivity cells are often not effectively employed with solid electrolytes particularly solids produced in situ, e.g., by curing of a liquid with ultraviolet radiation or an electron beam, due to the difficulty in removing the solidified electrolyte from the conductivity cell.

Furthermore, traditional conductivity cells can not be effectively employed to measure transport properties of solid electrolytes such as transference number and diffusion coefficient. Each of these properties can only be effectively measured when the electrolyte is sectioned which sectioning is difficult, if not impossible, to accomplish with traditional cells.

Moreover, in such environments, it would be preferable if the cell, or at least the chamber containing the electrolyte, was disposable.

SUMMARY OF THE INVENTION

The present invention is based in part upon the surprising discovery that a test cell having a longitudinal, well defined geometry is capable of being employed in measuring both the conductivity and transport properties of a solid electrolyte.

In one aspect, the present invention relates to the test cell which comprises a generally longitudinal shaped chamber, e.g., a cylinder, which includes a pair of rod-shaped electrodes and means for holding the electrode in place, e.g., one or more O-rings, which can also serve to maintain contact between the electrolyte and the active surface of the electrode.

In this regard, the electrode and holding means define a volume for holding a liquid and/or solid to be tested.

In another aspect, the present invention relates to a method for measuring the conductivity and/or transport properties of an electrolyte within the inventive test cell.

BRIEF DESCRIPTION OF THE DRAWINGS

FIG. 1 illustrates an electrochemical test cell according to the present invention;

FIGS. 2a–2c relate to an electrode which can be employed in the test cell of the present invention.

DETAILED DESCRIPTION OF THE PREFERRED EMBODIMENTS

The present invention is based in part upon the surprising discovery that the conductivity and transport properties of an electrolyte, and in particular a solid electrolyte, can be effectively measured by a single, disposable test cell.

The test cell according to the present invention includes a generally longitudinal chamber having a well-defined shape.

In this regard, "well defined" relates to a chamber that has a generally regular geometric shape. In particular, it is desired that the longitudinal chamber have the same thickness throughout its length. For example, where a cylinder is employed, it is desired that the circular cross-section of the cylinder have the same diameter through the length of cylinder. Other suitable cross-sectional shapes for the chamber include rectangles, squares and triangles. However, a circular cross-section, and thus a cylindrical shape for the chamber, is preferred.

Moreover, the chamber can be made of any material of construction which is sufficiently inert to the solid and/or liquid being tested.

Although non-insulating materials such as metal can be employed in the production of a chamber, it is preferred that the material of construction be a plastic such as polypropylene and Teflon®, or a ceramic material.

Plastic materials such as polypropylene are preferred due to cost and other practical considerations.

For example, if the electrolyte is a solid electrolyte to be cured in situ, then the chamber is preferably made from material such as polypropylene which is transparent to the curing technique employed, e.g., ultraviolet radiation. Furthermore, plastic materials are often preferred because their ability to be effectively cut up in order to section the solid electrolyte, which is preferred in measuring certain transport properties of the electrolyte.

In one embodiment, the chamber has a general cylindrical shape and is produced by cutting the tip off of a plastic syringe.

The test cell also includes a pair of electrodes each comprising an electrical conductive support having an active surface thereon.

The electrical conductive supports which can be employed include those which are recognized in the art and are dependent upon the particular conductivity cell. Preferably, a longitudinal, e.g., a rod-shaped electrode support is employed.

Suitable materials for such electrodes include stainless steel, Ni, Cu and brass with stainless steel being preferred.

In addition to metals, the electrode can be made of any electron conductive materials including semiconductors, conductive polymers including both intrinsic and carbon-loaded conductive polymers.

Moreover, the electrodes may either be blocking or non-blocking, i.e., non-reactive or reactive towards the electrolyte.

The "active surface" of an electrode in a conductivity cell is generally that portion of the surface of the electrode which is in electrolytic contact with the electrolyte. Suitable materials for the active surface include lithium, lead, as well as stainless steel.

The active surface of the electrodes employed in the present invention can preferably have a high surface area material thereon in order to provide for results which have the desired degree of accuracy. Furthermore, the active surface is preferably chemically inert to both the liquid and solid electrolytes to be tested.

An example of such a material for use with electrodes is a high surface area form of platinum, known as platinum black which can be produced, for example, by a plating process. In addition, copending application Ser. No. 08/049,062 (Atty Docket No. 1127), now abandoned, entitled "An Electrode for Conductivity Cells Comprising High Surface Area Metal Foil" discloses the use of a high surface area nickel or copper foil.

The test cell further includes means for holding the electrode in place, which means also preferably serve to define a volume for containing the electrolyte in the chamber and aids in maintaining contact between the electrolyte and the electrode surface. The means can further serve to render this volume adjustable, i.e., its size can be selected based upon the desired electrolyte, etc.

Suitable means are dependent upon, e.g., the shape and size of the chambers, the electrode, and the desired volume and would be recognized by those skilled in the art.

For that preferred embodiment employing a cylindrical barrel and a rod-shaped electrode, this means preferably comprises at least one, and preferably a pair, of O-rings.

The O-rings can be made of any material which is inert to the electrolyte. Examples of suitable materials include insulating materials such as rubber.

Other suitable means include the use of an insulating tape which can be wrapped around the electrode. It is preferred that such tape also be inert to the electrolyte. Suitable materials for the tape include Teflon®.

One particularly preferred embodiment of the test cell according to the present invention is illustrated in FIG. 1.

This cell comprises a chamber, 3, adapted from a plastic syringe by cutting off the tip of the barrel, and a pair of stainless steel rods, 4, each having at least one O-ring 5, located thereon, to contain the electrolyte, 1, and maintain contact with the electrode surface, 2.

Examples of preferred electrodes for use in the present invention are illustrated by FIGS. 2a–2c. FIG. 2a illustrates a rod-shaped electrode, 4, having a pair of O-rings, 5, which can be employed in the test cell according to the present invention.

FIG. 2b illustrates the end of one electrode in which a stainless steel rod, 4, has a suitable recess, 6, for introduction of an electrode, e.g., a lithium electrode, while FIG. 2c illustrates another embodiment in which an aluminum rod, 4, has an electrode, 7, e.g., a lead electrode, attached to the end thereof.

The test cell according to the present invention can be used in measuring the properties of virtually any liquid and/or solid.

In one preferred use for the test cell, a sample of unpolymerized electrolyte (liquid) can be placed into the chamber and sealed between the two electrodes. The conductivity of the liquid sample can then be measured. This sample can then be cured in situ by employing, e.g., ultraviolet radiation or an electron beam. The curing process converts the liquid electrolyte to a solid electrolyte which can be suitable for use, e.g., as an electrolyte in a solid battery.

The choice of electrolyte is not critical to the present invention.

Suitable solid electrolytes for use in solid state secondary batteries are described, e.g., in U.S. Pat. No. 4,925,751, the disclosure of which is incorporated herein by reference in its entirety.

In addition to allowing the effective measurement of conductivity, because the cell has a well defined geometry, e.g., a cylinder, it is capable of measuring transport properties of electrolytes.

Typical transport property measurements include the measurement of transference number and diffusion coefficient. These properties are typically measured subsequent to the sectioning of the electrolyte.

In fact, when suitable materials, e.g., plastic syringes are employed in producing the test cell, the solid electrolyte can be easily cut into sections which enables a detailed analysis of the electrolyte so as to determine any variation in properties which may exist through the length of the cell.

Due to the relatively low cost of certain materials of construction, particularly the chamber, e.g., plastics and certain metals, the test cell can be disposable.

While the invention has been described in terms of various preferred embodiments, the artisan will appreciate the various modifications, substitutions, and omissions, and changes that may be made without departing from the spirit thereof.

I claim:

1. A test cell for measuring conductivity and transport properties of a material comprising:
   (a) a generally longitudinal chamber having substantially the same thickness throughout its length;
   (b) a pair of electrodes, each comprising
      (i) a rod-shaped support having an active surface on at least a portion of one end of the support; and
      (ii) means for holding the electrode in place in the chamber, wherein the active surface and holding means of one electrode are in one end of the chamber and the active surface and holding means of the other electrode are in the other end of the chamber, and further wherein the holding means positions those ends of the electrodes which contain the active surface so as to define a volume in the chamber for holding a material to be tested and such that the active surfaces are in contact with the material.

2. The test cell according to claim 1 wherein the chamber has a cylindrical shape.

3. The test cell according to claim 2 wherein the chamber comprises at least one of a plastic, a ceramic and a metal.

4. The test cell according to claim 3 wherein the chamber comprises a plastic.

5. The test cell according to claim 4 wherein the chamber comprises polypropylene.

6. The test cell according to claim 3 wherein the chamber is produced by cutting off the tip of a plastic syringe.

7. The test cell according to claim 1 wherein each electrode comprises at least one of a metal, semiconductor, or a conductive polymer.

8. The test cell according to claim 7 wherein the electrode is a blocking electrode.

9. The test cell according to claim 7 wherein the electrode is a non-blocking electrode.

10. The test cell according to claim 1 wherein the active surface has a high surface area material thereon.

11. The test cell according to claim 1 wherein the active surface comprises lithium, lead, or stainless steel.

12. The test cell according to claim 1 wherein the holding means comprises at least one O-ring.

13. The test cell according to claim 12 wherein the holding means comprises at least two O-rings.

14. A method for measuring the conductivity or transport properties of a material comprising:
   (a) introducing a liquid and solid material into the chamber of a test cell which test cell is a cell according to claim 1; and
   (b) measuring the conductivity or a transport property of the material.

15. The method according to claim 14 wherein a solid is formed in situ in the test cell.

16. The method according to claim 15 wherein a curable liquid is introduced into the test cell.

17. The method according to claim 16 wherein the liquid is then cured by irradiation with UV radiation.

18. The method according to claim 16 wherein the liquid is then cured with an electron beam.

19. The method according to claim 16 wherein the conductivity of the liquid is measured before curing and the conductivity of the solid is measured subsequent to curing.

20. The method according to claim 19 wherein transport properties of the solid are measured subsequent to curing.

21. The test cell according to claim 1 wherein the chamber comprises a material which is transparent to UV radiation.

22. The test cell according to claim 1 wherein the chamber has a regular geometric cross-sectional shape.

* * * * *